12# United States Patent [19]

McQuigg et al.

[11] Patent Number: 5,015,706

[45] Date of Patent: May 14, 1991

[54] POLYMER-SUPPORTED 4-(N-BENZYL-N-METHYLAMINO)PYRIDINE CATALYST AND PROCESS FOR SAME

[75] Inventors: Donald W. McQuigg, Mooresville, Ind.; Heather K. Webb, Champaign, Ill.; Edward E. Sowers, Mooresville, Ind.

[73] Assignee: Reilly Industries, Inc., Indianapolis, Ind.

[21] Appl. No.: 247,152

[22] Filed: Sep. 21, 1988

[51] Int. Cl.$^5$ .............................................. C08T 2/08
[52] U.S. Cl. ..................................... 526/200; 526/258
[58] Field of Search ................................. 526/200, 258

[56] References Cited

U.S. PATENT DOCUMENTS 3,862,924  1/1975  Hamann et al. .................. 526/200
3,941,729  3/1976  Klein ................................ 526/200
4,091,054  5/1978  Saito et al. ....................... 526/200

OTHER PUBLICATIONS

Hofle, G., Steglich, W., Vorbruggen, H., *Angew. Chem. Int. Ed. Engl.*, 17, 569 (1978).
Scriven, E. F. V., *Chem. Soc. Rev.*, vol. 12, No. 2 (1983).
Frechet, J. M. J., Deratini, A., Darling, G., Lecavalier, P., Li, N. H., *Macromol. Chem. Macromol. Symp.*, 1, 91 (1986).
Patchornik, A., *Chemtech*, Jan., 1987, 58.
Hierl, M. A., Gamson, E. P., Klotz, I. M., *J. Am. Chem. Soc.*, 101, 6020 (1979).
Delaney, E. J., Wood, L. E., Klotz., I. M., *J. Am. Chem. Soc.*, 104, 799 (1982).
Klotz, I. M., Massil, S. E., Wood, L. E., *J. Polymer Sc., Polymer Chem. Ed.*, 23, 575 (1985).
Guendouz, F., Jacquier, R., Verducci, J., *Tetrahedon Lett.*, 25, 4521 (1984).
Shinkai, S., Tsuji, H., Hara, Y., Manabe, O., *Bull. Chem. Soc. Jpn.*, 54, 631 (1981).
Tomoi, M., Akada, Y., Kakiuchi, H., *Macromol. Chem., Rapid Commun.*, 3, 537 (1982).
Deratani, A., Darling, G. D., Horak, D., Frechet, J. M. J., *Macromolecules*, 20, 767 (1987).
Deratani, A., Darling, G. D., Frechet, J. M. J., *Polymers* (1987 in press).
10th Intl. Conf. Heterocycl. Chem. (1985).
Tomoi, M., Goto, M., Kakiuchi, H. J., *Polym. Sc., Polym. Chem.*, 25, 77 (1987).
Storck, W., Manecke, G., *J. Mol. Cat.*, 30, 145 (1985).
Koning, C. E., Eshuis, J. J. W., Viersen, F. J., Challa, G., *Reactive Polym.*, 4, 293 (1986).
Menger, F. M., McCann, D. J., *J. Org. Chem.*, 50, 3928 (1985).

*Primary Examiner*—Joseph L. Schofer
*Assistant Examiner*—Alex H. Walker
*Attorney, Agent, or Firm*—Woodard, Emhardt, Naughton, Moriarty & McNett

[57] ABSTRACT

A cross-linked polymer-supported 4-(N-benzyl-N-methylamino) pyridine material and process for its preparation in high yield and having effective physical and catalytic properties. The polymer-supported catalyst is characterizd by the suspension copolymerization of an organic phase containing the corresponding vinyl-substituted pyridine monomer, a styrene monomer, and a suitable cross-linking agent and free radical-generating catalyst in the presence of an aqueous phase containing a cellulose ether derivative as the stabilizing agent. The catalyst is further characterized by its yield in excess of 90% by weight and by its predominant and generally spherical and smooth bead form and substantially uniform size that is efficiently hard and durable and possesses sufficient catalytic activity for effective use in acylation, alkylation or other related reactions.

2 Claims, No Drawings

POLYMER-SUPPORTED 4-(N-BENZYL-N-METHYLAMINO)PYRIDINE CATALYST AND PROCESS FOR SAME

BACKGROUND OF THE INVENTION

This invention relates generally to polymer-supported catalysts having pyridylamino functionality, and in particular to a cross-linked copolymer of vinyl substituted 4 (N benzyl-N methylamino)pyridine and a styrene monomer derivative characterized by improved physical properties and marked catalytic activity, and to the process for preparing the same.

By way of general background, it has been recognized for some time that 4 dimethylaminopyridine (commonly referred to as "DMAP") and certain of its dialkylamino analogs are highly effective catalysts for acylations, alkylations and other related reactions. Hofle, G., Steglich, W., Vorbruggen, H., *Angew. Chem. Int. Ed. Engl*, 17, 569 (1978); Scriven, E.F.V., *Chem. Soc. Rev.,* 129 (1983). Also recognized for some time has been the desirability of a polymer bound or supported version of such DMAP like catalysts in view of the potential advantages of ease of recovery and repeated use along with the adaptability of such catalysts in both static and flow systems. Although such polymers could be soluble, it is understood that insoluble, heterogeneous gel or macroreticular resin beads provide the greater advantages in ease of removal and recyclability. Fréchet, J.M.J., Deratini, A., Darling, G, Lecavalier, P., Li, N.H., *Macromol. Chem. Macromol. Symp..* 1, 91 (1986); Patchornik, A., *Chemtech,* Jan., 1987, 58.

Accordingly, much investigation has taken place in search of an effective polymer supported DMAP like catalyst. For example, Klotz and his coworkers were the first to report such a polymer made by attaching an acid functionalized dialkylaminopyridine to a polyethyleneimine polymer. Hierl, M.A., Gamson, E.P., Klotz, I.M., *J. Am. Chem. Soc.,* 101, 6020 (1979). Klotz in combination with others subsequently reported similar functionalized polyimines, and demonstrated their catalytic ability by kinetic experiments on the hydrolysis of p-nitrophenyl caproate Delaney, E.J., Wood, L.E., Klotz., I.M., *J. Am. Chem. Soc.,* 104, 799 (1982); Klotz, I.M., Massil, S.E., Wood, L.E., *J. Polymer Sc., Polymer Chem. Ed.,* 23, 575 (1985). These polymers suffered, however, from the drawback that the pyridine was attached to the polymer backbone by an amide linkage which was susceptible to scission as when regenerating the resin using sodium hydroxide in acetylation reactions involving acyl halides.

Verducci and his coworkers reported attaching 4-piperidinylpyridine, among other DMAP like moieties, to a Merrifield resin also through an amide bond. Guendouz, F., Jacquier, R., Verducci, J., *Tetrahedon Lett.,* 25, 4521 (1984). The amide bond 1n this polymer, however, was reported to stand up well on recycle in the catalytic acetylation of 1-methylcyclohexanol at 70° C. and 24 hours.

Nevertheless, more popular approaches to achieve DMAP-like polymer catalysts have avoided the us of amide linkages altogether. For example, Shinkai and his coworkers reported attaching 4-chloropyridine to an aminomethylpolystyrene to yield a polymer-supported 4-(N benzyl N-methylamino)pyridine (which functional group has commonly become known as "BMAP"). Shinkai, S., Tsuji, H., Hara, Y., Manabe, O., *Bull. Chem. Soc. Jpn.,* 54, 631 (1981). This polymer-bound BMAP material was reported to effectively catalyze simple esterifications, but the product achieved by Shinkai had the disadvantages of including a high percentage of a secondary amine which interferred with the reaction unless alkylated prior to use.

Another group of investigators led by Tomoi has compared two other approaches to achieve a similar polymeric BMAP catalyst. Tomoi, M., Akada, Y., Kakiuchi, H., *Macromol. Chem.. Rapid Commun.,* 3, 537 (1982). Tomoi reported, among other things, that a route involving copolymerization of the preformed BMAP monomer gave a better catalyst product. However, more recently a group led by Fréchet challenged this conclusion, reporting that preformed chloromethylated polystyrene can be modified readily and quantitatively to produce an even better catalyst. Fréchet, J.M.J., Deratini, A., Darling, G, Lecavalier, P., Li, N.H., *Macromol. Chem. Macromol. Symo.,* 1, 91 (1986). Menger and his coworkers have also reported success in converting a linear chloromethylpolystyrene resin to the corresponding linear BMAP polymer which has proven effective in well known DMAP catalyzed processes such as the conversion of linalool to linalyl acetate which has definite commercial interest. Menger, F.M., McCann, D.J., *J. Org. Chem.* 50, 3928 (1985).

The extent of work in this field has also led groups headed by Fréchet, Tomoi, Manecke and Challa to study the effects of variation of the frequency of BMAP-to-styrene units as well as variations of cross-linking and of the length and nature of the spacer arm or component separating the pyridylamino functional group from the polymer backbone. To this end, numerous polymers have been reported by these groups with varying degrees of detail. Deratani, A., Darling, G.D., Horak, D., Fréchet, J.M.J., *Macromolecules,* 20, 767 (1987); Deratani, A., Darling, G.D., Fréchet, J.M.J., *Polymers* (1987 in press); 10th Intl. Conf. Heterocycl. Chem. (1985); Tomoi, M., Goto, M., Kakiuchi, H.J., *Polym. Sc., Polym. Chem.,* 25, 77 (1987); Storck, W., Manecke, G., *J. Mol. Cat.,* 30, 145 (1985); and Koning, C.E., Eshuis, J.J.W., Viersen, F.J., Challa, G., *Reactive Polym.,* 4, 293 (1986).

In reviewing these collective efforts, as highlighted above, it is evident that the paramount interest to date has been to confirm the ability to synthesize polymer-supported catalysts of these types approaching DMAP activity. Accordingly, little or no effort has gone into characterizing in a quantitative or qualitative way the physical or chemical properties of the polymer compounds thus far obtained. Nevertheless, these same properties dictate the ultimate commercial utility of such polymeric catalysts in whatever reactions they are used.

For example, while these considerable scientific publications have demonstrated the general or potential utility of polymeric catalysts of this type, nearly all have done so with polymers having low degrees of cross linking up to only about 2% by weight of the total polymerizable monomer present. These prior art polymers have been reported and proven to be mechanically weak and to exhibit noticeable breakage and disintegration both as formed and during use, particularly with even moderate attempts at recycling. In addition, these polymers have exhibited substantial swelling in excess of 100–200% by volume upon exposure to a solvent which has aggravated breakage upon recapture. This is a definite disadvantage in many commercial processes, for example, where space constraints are important.

Moreover, these polymers prepared according to the literature references contain significant amounts of granular powders, flake or other irregular shapes instead of the predominant bead form that is preferred. Such unwanted particles are mechanically unstable and suitable for use only in stirred-slurry or other reactors where clogging of filters or lines is not a concern and where recycling of the catalyst is not contemplated. The gel type bead segments that are present in these reference materials are nonuniform in size or configuration, exhibit great deviation from the average or median size present, and do not show the durable, hard form that is preferred. While Fréchet has reported making a 34% divinylbenzene (DVB) cross linked macroreticular resin also within this class, he reported and subsequent testing has confirmed that it has inferior chemical and physical properties as a catalyst in the acylation of 1-methylcyclohexanol. In addition, Fréchet's resin made from his preferred chloromethylated polystyrene process may contain quaternary salt from unwanted side reactions which can react to ring-open under strongly basic conditions as often encountered.

Therefore, while certain publications have reported the synthesis of polymer supported DMAP-like resins and their general catalytic ability, there has been and remains today the need for a catalyst of this type in both gel and macroreticular form that exhibits overall mechanical stability as expected with higher degrees of cross linking while retaining effective chemical properties believed lost in such materials. Improved physical properties of surface texture and configuration, uniformity and durability are also desired, as are chemical properties approaching the catalytic potency and universal acceptance of DMAP and its analogs.

SUMMARY OF THE INVENTION

The applicants' present invention addresses these needs in the discovery of a cross-linked polymer supported 4(N-benzyl N methylamino)pyridine material having superior physical properties and highly active and effective as a catalyst for acylation, alkylation and other related reactions. This polymeric BMAP catalyst is prepared through the free radical suspension copolymerization of an organic phase comprising the vinyl-substituted BMAP monomer, a styrene monomer and a suitable free radical-generating catalyst and cross-linking agent in the presence of a selected aqueous suspending medium.

In its preferred form, this polymer supported BMAP material is characterized by its generally spherical and smooth bead form and substantially uniform size ranging up to about 1.0 mm in diameter and exhibiting minimal deviation from the median or average bead size in a given batch. The beads are hard and durable, being both easily recoverable following copolymerization and readily recyclable in use. The beads may have a gel or a macroreticular structure, as desired, depending upon the degree of cross linking and other factors such as the presence of a suitable diluent such as an organic solvent in the copolymerization process The beads are also characterized by the absence of any significant amount of granular powders, flake or other irregular particles either as originally formed or as the result of unwanted deterioration from normal catalytic use. The beads have further shown to have highly effective catalytic activity approaching that of DMAP in the reactions tested.

Still further, this preferred polymer-supported BMAP material is characterized by its suspension copolymerization process and, in particular, by the use of an aqueous phase comprising a cellulose ether derivative as the stabilizing or suspending agent. With this preferred suspension component, high percentages of the desired polymer beads have been recovered in excess of 90% by weight of the total product which exhibit the surprisingly superior physical properties of shape, size, hardness and overall quality and appearance described herein while also demonstrating unexpected and effective catalytic utility also described.

Related objects and advantages of the present invention will be apparent from the following description.

DESCRIPTION OF THE PREFERRED EMBODIMENT

For the purposes of promoting an understanding of the principles of the invention, reference will now be made to the several embodiments and specific language will be used to describe the same. It will nevertheless be understood that no limitation of the scope of the invention is thereby intended, such alterations and further modifications in the device, and such further applications of the principles of the invention as illustrated therein being contemplated as would normally occur to one skilled in the art to which the invention relates.

In accordance with the above, the applicants have discovered a commercially significant DMAP-like polymer resin containing 4 methylaminopyridine groups functionally bound to a cross-linked styrene backbone at the 4-amino site through a vinylbenzyl linkage. The preparative process of choice comprises the suspension copolymerization of vinyl substituted 4-(N benzyl N-methylamino)pyridine with a styrene monomer and a suitable cross-linking agent and free radical generating catalyst. This is contrasted by the indirect method reported in the literature which involves subsequently attaching 4-pyridineamine groups to a preformed chloromethylated polystyrene resin. The applicants found that this indirect method incorporated less of the pyridylamino functional groups incorporated onto the preformed polymer and required longer reaction times with more likelihood of contamination from quaternary salt formation or other residual presence of the chloromethyl component. In any case, the preferred polymer resins of the invention have been identified by infrared (I.R.) and elemental combustion analysis and their catalytic activity has been confirmed by reactions such as those reported in Example 4 below involving a Fries ester rearrangement and the acetylation of 1-methylcyclohexanol. In each reaction, the applicants' heterogeneous polymeric catalyst performed effectively and compared favorably with DMAP used under homogeneous conditions.

Referring further to the process embodiment of the invention, the terms "free radical suspension copolymerization" are well known to those skilled in this art and comprise the process of polymerizing a comonomer mixture which has been suspended in the form of droplets in a medium of some composition in which the monomers are at least substantially insoluble. The discrete nature of these droplets and the size and stability of the suspension depend in large part on the nature of the medium used including its individual components or additives, as well as on various physical factors in the procedure such as stirring rate, temperature and the like. The medium used in this invention is an aqueous phase suspension of a particular class of stabilizing agent as described below.

As the copolymerization proceeds, these droplets appear and take on various forms which will affect their physical and chemical properties in later use. Although it is common to refer to all such polymer droplets as "beads," in fact they may range from granular powders, flake or other irregular shaped particles such as produced by the prior art processes discussed above to the predominantly uniform and smooth, hard spherical beads achieved by the applicant's invention.

One method of promoting the copolymerization is to provide a suitable catalyst which when elevated to a sufficient temperature will decompose to provide free radicals which function as initiators for the reaction. Two general classes of such free radical generating catalysts are known, those being peroxides and azo compounds. The selection of an initiator within these groups, and its amount and method of use, is within the knowledge and skill of the art and depends on availability, on the specific comonomer mixture used and on other factors affecting the reaction. The catalyst used in the applicants' work has been an azo compound identified as 2,2'-azobis-(2,4 dimethylvaleronitrile) and marketed by E. I. du Pont de Nemours & Company (DuPont) under the trademark Vazo 52. The preferred range of this catalyst has been from about 0.1–1.0% by weight of the total comonomer components used. It is nonetheless understood that other catalysts within these groups are similarly suited for this purpose and are within the scope of the invention.

As the copolymer of the applicants' invention is an insoluble or heterogeneous material, a suitable cross linking agent must also be included in the organic component during the copolymerization process. Many such cross linking agents are commercially available, and their utility and interchangeability in reactions such as the process at hand are well known to those skilled in this art. The applicants have to date used a commercial divinylbenzene (commonly referred to as "DVB") for this purpose in amounts varying according to the desired physical structure of the reaction product as further discussed below. In any case, however, it is understood that other suitable cross-linking agents are known to exist and are within the scope of the invention.

The reaction conditions for the preferred process such as the temperatures and times for the copolymerization to occur as well as appropriate equipment and procedures such as the desirability of agitation and the like are also well known to those practiced in this art. Accordingly, the same require little further elaboration in this specification. For example, it is known that the temperature to initiate polymerization depends as a practical limit on the decomposition temperature of the free radical-generating catalyst used. As some reactions in this class are exothermic, little or no additional heating is necessary although some may be desirable at later stages to assure complete copolymerization of the monomer present. For the applicants' preferred Vazo 52 catalyst, an initiation temperature of about 55° C. was employed with an elevated temperature of about 85° C. used to finish off the reaction. With other suitable catalysts, this initiation temperature may increase or decrease significantly coupled with completing the reaction at temperatures up to or at reflux of about 100° C. or above. It is similarly known, for example, that oxygen inhibits these reactions and was therefore kept from the system in the Examples below by maintaining a nitrogen purge during the copolymerization process.

Referring now to a second embodiment, the cross linked polymer supported BMAP material in accordance with the invention is characterized by being suspension copolymerized in the presence of a particular aqueous phase which comprises a cellulose ether derivative as the stabilizing or suspending agent. Suitable cellulose ether derivatives (and examples of their available commercial trademarks and sources) include methylcellulose (such as Methocel A from Dow Chemical Corporation of Midland, Michigan and Culminal from Aqualon Company of Wilmington, Delaware); hydroxyethylcellulose (such as Natrosol 250 from Aqualon and Cellosize from Union Carbide Corporation of Danbury, Connecticut); hydroxypropylcellulose (such as Klucel J from Aqualon); hydroxypropyl methylcellulose (such as Methocel E, F, J and K and 50 123 from Dow Chemical and Culminal MHPC from Aqualon); hydroxyethyl methylcellulose (such as Culminal from Aqualon); carboxymethyl methylcellulose (such as CMMC from Aqualon); hydrophobically-modified hydroxyethylcellulose (such as HMHEC WSP-M 1017 from Aqualon); carboxymethyl hydroxyethylcellulose (such as CMHEC 37L from Aqualon); and hydroxypropyl hydroxyethylcellulose (such as Natrovis from Aqualon). In many cases, these trademarks represent classes or series of compounds offered by these companies which will work effectively in the present process. Moreover, this listing of cellulose ether derivatives is not exhaustive as there are other such derivatives both naturally-occurring and synthetic which are also suited for this purpose and are within the scope of the invention.

The amount required of this stabilizing additive in the aqueous phase to effect the desired copolymerization of the present invention will vary according to the cellulose ether used as well as other factors. From work thus far some preference has been shown for hydroxypropyl methylcellulose (such as Methocel 50 123 from Dow Chemical), hydrophobically modified hydroxyethylcellulose (such as HMHEC WSP M 1017 from Aqualon) and carboxymethyl hydroxyethylcellulose (such a CMHEC 37L from Aqualon) in preferred concentrations up to about one-half percent (0.50%) by weight of the total aqueous phase. Most preferred have been concentrations of about one tenth percent (0.10%) by weight. The limiting factors in selecting these derivatives and amounts are practical ones such as availability and ease of use and process concerns affecting viscosity and the proper maintenance of the suspension once achieved. In any case, the use of these cellulose ether derivatives in the aqueous phase of the present invention has yielded superior copolymer beads having effective physical properties as well as highly active catalytic functionality. These results were unexpected and are a significant improvement over the additives reported in the literature for preparing similar polymer-supported DMAP like catalysts.

The selection of materials for the organic monomer phase in accordance with the invention first involves preparing the vinyl substituted 4(N-benzyl N-methylamino)pyridine (BMAP) monomer through the reaction of 4-(N-methylamino)pyridine with vinylbenzylchloride as reported in the 1982 Tomoi article previously referenced. Also present is a styrene monomer component including styrene itself and/or substituted styrene derivative such as ethylstyrene which is similarly suited for this purpose and is within the scope of the invention. Still further, there is a suitable free radical generating catalyst and cross linking agent in accordance with the descriptions above.

The concentration and ratio of these monomer materials in the organic phase will vary appreciably depending upon the desired physical and chemical characteristics of the resulting copolymer product. BMAP loading is a convenient measure as the amount of pyridylamino groups present has a direct relationship to the functioning of the copolymer resin as a catalyst in acylation, alkylation or other related reactions. For example, the preferred polymer supported material has been successfully prepared in accordance with the invention across a wide range of BMAP loading up to about 50% by weight of the BMAP monomer compared to the total monomer present in the organic phase. This is approximately equivalent to a mole percent up to about 33% and to molar ratio up to about 1:2 of BMAP monomer to total styrenic monomer in the organic phase. In this regard, the term "total styrenic monomer" is meant to include styrene and any styrene derivatives such as ethylstyrene and divinylbenzene, and is in deference to the fact that commercial DVB cross-linking agent is a styrene derivative having some unreacted ethylstyrene component. For example, the 55% DVB used in the Examples below typically has about 45% ethylstyren remaining in the material. This entire DVB component including the extraneous styrenic material is included in the BMAP loading calculation. In a similar manner, the most preferred BMAP loading from work performed to date is about 34% by weight of BMAP monomer compared to total styrenic monomer in the organic phase, which equates to about 20 mole percent and to a molar ratio of about 1:4.

As alluded to earlier, the amount of agent such as divinylbenzene in the organic monomer phase directly affects the degree of cross linking and to a large extent both the physical and chemical properties of the resulting copolymer catalyst product. With this in mind, decreasing concentrations of DVB below about 8-10% by weight in accordance with the invention has produced effective gel resins that are generally translucent and hard, durable beads in appearance and exhibit increasing swellability and accompanying activity typical of lower degrees of cross linking. Increasing concentrations of DVB above about 8-10% by weight, on the other hand, has produced similarly effective gel resins that are general harder bead forms less subJect to swelling or disintegration during use and exhibit some possible loss of accompanying activity typical of such higher degrees of cross linking. By increasing still further the concentration of DVB coupled with the inclusion of a suitable diluent such as an organic solvent in the monomer phase during copolymerization, the resulting product has been effectively changed from a gel to a macroreticular bead form as determined by the presence of a permanent pore structure and opaque appearance typical of such resins upon later removal of the solvent. Although many suitable solvents exist for this purpose, the applicants have employed a VMP Naphtha material distributed by Chem Central of Indianapolis, Indiana in about 33% by weight of the total organic phase. As shown in Example 4 below, the applicants' preferred polymeric material has shown effective catalytic properties at 15% cross-linking in both gel and macroreticular forms. Selection of the appropriate cross linking and resin form for a given catalytic reaction, including the nature and amount of any solvent used, is well within the knowledge and skill of those practiced in this art and is within the scope of the present invention.

Referring to still a third embodiment, the cross-linked polymer-supported BMAP material of the invention is further characterized and distinguished from the art by the same physical and catalytic properties which have been surprisingly discovered. In particular, the preferred copolymer material has been prepared in high yield well in excess of 90% of the total recovered product. More importantly, the preferred material has shown little or no evidence of clumping or of the presence of granular powders, flake or other irregular material to hamper later use or recycling of the catalyst. On the contrary, the preferred material has exhibited a generally smooth and spherical bead form with the further advantage of a substantially uniform size distribution ranging up to about 1.0 mm in diameter and a minimal deviation from the median or average bead size in a given reaction. Subsequent testing has shown these same preferred copolymer beads resist attrition as a result of swelling in the case of gel resins and overall are hard, highly durable and easily recyclable in both gel and macroreticular forms. These beads have further shown surprisingly effective catalytic activities approaching those of DMAP in reactions tested as highlighted in Example 4 below, but with the added advantages attendant their heterogeneous structure.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

SUSPENSION COPOLYMERIZATION PROCEDURE

The following is the procedure used by the applicants in preparing the polymer-supported BMAP catalyst materials according to the previously described embodiments of the invention:

An aqueous phase was first prepared using water and one of the cellulose ether derivatives listed in Example 2, as the stabilizing or suspending agent. 150ml of this aqueous phase was added to a 300 ml roundbottom flask fitted with a condenser, nitrogen purge ports, a thermometer and a stirrer equipped with a glass stirring shaft and Teflon blade. The aqueous solution was purged with nitrogen, stirred and brought to the appropriate reaction temperature to permit free radical generation by the catalyst being used (with Vazo 52, this was about 55° C.). Approximately 30 g of one of the organic monomer phases also listed in Example 2 was then added to the stirred aqueous phase below the liquid surface through a long-necked funnel. The resulting dispersion was maintained at the reaction temperature (about 55.C.) with continued stirring and nitrogen purge for 3 hours until the copolymerization was substantially complete. The dispersion was then heated to about 85° C. and maintained at that temperature for 16 hours with continued stirring and nitrogen purge to finish off the reaction, followed by cooling to room temperature. The insoluble cross-linked polymex supported BMAP resin beads were removed from the remaining liquid by filtration, rinsed and dried, then their identification and composition confirmed through infrared (I.R.) and elemental combustion analysis.

EXAMPLE 2

Aqueous and Organic Phase Preparations

For use in the procedure of Example 1, aqueous phase solutions were prepared in accordance with the invention using each of the cellulose ether derivatives previously identified in the specification as the stabilizing or suspending agent. These included methylcellulose (such as Methocel A from Dow Chemical Corporation of Midland, Michigan and Culminal from Aqualon Company of Wilmington, Delaware); hydroxyethylcellulose (such as Natrosol 250 from Aqualon and Cellosize from Union Carbide Corporation of Danbury, Connecticut); hydroxypropylcellulose (such as Klucel J from Aqualon); hydroxypropyl methylcellulose (such as Methocel E, F, J and K and 50-123 from Dow Chemical and Culminal MHPC from Aqualon) hydroxyethyl methylcellulose (such as Culminal from Aqualon); carboxymethyl methylcellulose (such as CMMC from Aqualon); hydrophobically-modified hydroxyethylcellulose (such as HMHEC WSP-M 1017 from Aqualon) carboxymethyl hydroxyethylcellulose (such as CMHEC 37L from Aqualon); and hydroxypropyl hydroxyethylcellulose (such as Natrovis from Aqualon). The aqueous solutions were prepared according to the manufacturer's directions, and generally involved dispersing appropriate amounts of the additive in water at about 85° C. followed by cooling to room temperature to effect proper hydration.

Organic phases for use in the procedure of Example 1 were also prepared in accordance with the invention with varying concentrations of vinyl substituted BMAP monomer, with styrene itself as the styrenic monomer of choice, and with 55% DVB and Vazo 52 as the cross-linking agent and copolymerization catalyst. BMAP loading was varied at about 15%, about 20%, about 34% and about 50% by weight of the BMAP monomer compared to the total monomer component in the organic phase. This is approximately equivalent to a range of about 7.8 mol%, about 11 mol%, about 20 mol%, and about 33 mol% and to a range of molar ratio of about 1:11, about 1:8, about 1:4 and about 1:2 of BMAP monomer to total monomer present. For example, approximately 30 g of organic phase at 2% cross linking and 34% BMAP loading contained 11.2 g BMAP monomer, 1.18 g 55% DVB, 19.88 g styrene and 0.16 g Vazo 52. A similarly 4% cross linked material at 15% BMAP loading contained 3.73 g BMAP monomer, 1.82 g DVB, 18.93 g styrene and 0.12 g Vazo 52, at 20% BMAP loading contained 8.26 g BMAP monomer, 2.74 g DVB, 29.14 g styrene and 0.16 g Vazo 52, and at 50% BMAP loading contained 15.00 g BMAP monomer, 2.20 g DVB, 13.91 g styrene and 0.16 g Vazo 52. By way of further example, 30 g of organic phase at 4% cross linking and 34% BMAP loading contained 11.2 g BMAP monomer, 2.37 g 55% DVB, 18.94 g styrene and 0.16 g Vazo 52. Still further organic phases were prepared at these three levels of BMAP loading with varying amounts of DVB to prepare copolymer products at levels of cross linking increasing by 2% up to 12% by weight of the organic phase. These additional mixtures were prepared according to known procedures, but simply with stoichiometrically varying amounts of individual components to arrive at the concentrations desired.

EXAMPLE 3

Polymer-Supported BMAP Catalyst

Employing the suspension copolymerization procedure of Example 1 and the aqueous and organic phases of Example 2, the applicants prepared, isolated and identified by I.R. and elemental combustion analysis the polymer supported BMAP materials obtained from these reactions in accordance with the present invention. In each case, the copolymer yield was well in excess of 90% by weight of the total reactants and was characterized by a predominant and generally smooth and spherical bead form and substantially uniform size ranging from up to about 1.0 mm in diameter with a minimal deviation in bead size in each yield. Each copolymer product was further characterized by the absence of clumping or any significant extraneous material such as the granular powders, flake and other irregular-shaped particles common to literature preparations. Still further, the bead form of each product was hard, durable and generally translucent giving the overall appearance of an effective gel resin for catalytic purposes. Microscopic examination of the copolymers showed no fractures or bubbles in the particle beads as formed. In subsequent testing repeated swellings in a toluene solvent and by stirring in a toluene slurry for more than 2 days, no significant fracturing of the recovered beads was found thereby confirming their durability and recyclability in a commercial setting.

Although preferences as to cross-linking, BMAP loading, the selection of the preferred stabilizing additive and the like will vary in practice depending on many factors, not the least of which is the particular catalytic reaction of interest, certain preferences have been identified at least under the procedures and reactions investigated to date. In this regard, the stabilizing additives most preferred have been Methocel 50-123, HMHEC and CMHEC 37L as previously described. The polymer-supported BMAP resins most preferred have similarly possessed a 34% BMAP loading with either 2% or 4% cross-linking.

EXAMPLE 4

Comparison of 15% Cross-Linked Gel & Macroreticular Resins

Initially phase prepared by heating 50 ml of water to about 85° C. in an appropriate vessel. With brisk stirring, 0.30 g of Methocel 50 123 was added and the mixture was stirred for about 5 minutes. 150 ml of cold water was added and the mixture was then cooled to room temperature with periodic stirring for about another hour to complete solvation of the stabilizing agent.

Two organic monomer mixtures were prepared using the following recipes: For the gel resin, 10.20 g BMAP monomer (as used in Example 2), 11.62 g styrene, 8.18 g 55% DVB and 0.15 g Vazo 52 were combined with stirring to give a homogeneous solution which was maintained at about 5° C. until its addition to the aqueous phase during copolymerization. For the macroreticular resin, the same procedure was followed using 10.2 g BMAP monomer, 11.62 g styrene; 8.18 g 55% DVB, 9.90 g VMP Naphtha and 0.16 g Vazo 52.

The suspension copolymerization of each monomer phase was then carried out according to the procedure of Example 1. Confirmation of each copolymer composition was by I.R. and elemental combustion analysis.

The gel resin appeared as translucent, generally spherical and smooth beads that were consistent with the overall physical properties of the other material described in the specification in accordance with the invention. The macroreticular resin similarly appeared as generally spherical and smooth bead particles also of a substantially uniform size and appearance, but with a whitish color consistent with the presence of substantial microporous channels throughout the bead structure characteristic of such materials. Porosity was confirmed by surface area measurements (ca. 30 m$^2$/g). Both polymer resins proved hard and durable when used in the following reactions and were then recovered for recycling in each case after washing with appropriate solvents to displace any residual water present.

Ester Rearrangement Study

For the purpose of testing and comparing the catalytic effectiveness of these 15% cross linked gel and macroreticular resins, a dimedone rearrangement reaction was studied in which 3-isobutyryloxy-5,5 -dimethyl-2 -cyclohexenone was converted to 2 isobutyryl-5,5 dimethyl 1,3cyclohexanedione. A stock solution of 21.03 g (0.1 mol) 3-isobutyryloxy-5,5-dimethyl-2-cyclohexenone with toluene was then prepared and filled to the line in a 100 ml volumetric flask. A 10 ml aliquot of the solution was pipetted into the test tube containing a 1:1 gram equivalent amount of either the gel or macroreticular resin catalyst prepared in the first part of this Example. The tube was placed in a constant-temperature bath at 100° C., and the reaction mixture was magnetically stirred for 25 hours with samples taken at various times. The gas chromatographic (GC) conditions were set at 12 m DBI @ 160.C. After the last sample was taken, the reaction mixture was left to filter for 2 hours and weighed. From the GC assay, the percent conversion based on the amount of starting material remaining was then calculated.

For the 15% cross-linked macroreticular resin catalyst, 75.7% conversion was detected after 4 hours and 97.5% conversion after 24 hours in the heated water bath. For the 15% cross linked gel material, 79.7% conversion occurred after 4 hours and 98.0% conversion after 24 hours of reaction. Similar testing and calculations were then made using homogeneous DMAP material. A comparison was made by dividing the percent conversion for the polymer supported BMAP material by the corresponding conversion using DMAP multiplied by 100 to convert to a percentage. This percent conversion comparison relative to DMAP for both the macroreticular and the gel resins was 79.0 and 83.2, respectively, after 4 hours and was 98.3 and 99.3%, respectively, after 24 hours. In each case, this reflects a effective result demonstrating the significant catalytic activity of the polymer supported BMAP material prepared in accordance with the invention relative to the known DMAP standard.

Acetylation of 1-Methylcyclohexanol Study

For the further purpose of testing and comparing the catalytic utility of these 15% cross-linked materials, a procedure similar to the ester rearrangement was used for the acetylation of 1-methylcyclohexanol. A stock solution was first prepared with 30 ml triethylamine (TEA) and 20 ml 1-methylcyclohexanol pipetted into 200 ml volumetric flask which was filled to the line with toluene. The polymer-supported BMAP catalyst (0.41 mmol, 5 mol%) was added to the culture tube and 10 ml of the stock solution which contained 1 ml (8.1 mmol) 1-methylcyclohexanol and 1.5 ml TEA (10.8 mmol) was also pipetted into the tube. After stirring 10 minutes in a 60.C. constant temperature bath, 1.5 ml acetic anhydride (15.8 mmol) was added to the tube. Stirring at 60° C. was continued and at various times, samples were taken for determining conversions. After 24 hours, the tube was removed from the hot chloroform bath, and the catalyst was washed with toluene, filtered off and dried for 2 hours. Visual inspection of both the gel and macroreticular resins showed that the beads had held up well during the reaction, with any deterioration evident being the result of the stirring method used in the experiment. It is understood that alternative stirring techniques such as used in Example 1 will eliminate catalyst breakage due to this cause.

Following GC analysis of the samples, it was determined that for the 15% cross linked macroreticular resin, 21.6% conversion to the acetate occurred after 6 hours while 37.1% was converted after 24 hours in the bath. For the 15% cross linked gel resin, the corresponding values were 25.4% conversion after 6 hours and 38.1% conversion after 24 hours. These conversions were then compared relative to similar DMAP-catalyzed reactions with the percent conversion relative to DMAP for the macroreticular resin being 27.1% after 6 hours and 38.4% after 24 hours, and for the gel resin being 31.9% and 39.4%, respectively. As with the ester rearrangement, this testing confirmed the effective catalytic activity of both the gel and macroreticular resins prepared according to the applicants' invention. This was true even with the high 15% cross linking in these resins which is substantially greater than may be desired under the circumstances of a particular reaction. As this cross-linking decreases, activity levels would increase both in absolute terms and relative to similar DMAP conversions.

EXAMPLE 5

Comparison of Aqueous Phases

Suspension copolymerizations were carried out in the manner described as follows comparing one of the preferred aqueous phases in the invention using Methocel 50-123 as the stabilizing additive against the aqueous phases reported by groups led by Tomoi (Tomoi, M., and Ford, W.T., *J. Am. Chem. Soc.,* 103, 3828 (1981)), and Fréchet (Deratini, A., Darling, G.D., Horak, D., and Fréchet, J.M.J., *Macromolecules,* 20, 767 (1987)) and comparing the preferred organic phase in the invention against the alternative recommended by Fréchet (Deratini, A., Darling, G.D., Horak, D., and Fréchet, J.M.J., *Macromolecules,* 20, 767 (1987)).

Preparation of Aqueous Phases

The Tomoi aqueous phase was prepared by mixing a solution containing 1.35 g gelatin, 12.5 g Merquat 100 (which is poly(diallyldimethylammonium chloride) marketed by Calgon Corp., Pittsburg, Pennsylvania) and 5.1 g boric acid in 450 g of water. Its pH was adjusted to 10.0 with a 25% aqueous solution of sodium hydroxide.

The Fréchet aqueous phase was prepared by simply dissolving 6.75 g polyvinylalcohol (Airvol 523 manufactured by Air Products and Chemicals, Inc. of Allentown, Pennsylvania) in 450 g of water.

The aqueous phase in accordance with the present invention which was in this test was prepared as described in Example 4.

Preparation of Organic Phases

Two organic phases were prepared for use in the comparison. The first involved subsequent attachment of 4-(N-methylamino)pyridine groups to a preformed cross-linked chloromethylated polystyrene. This procedure was preferred by Fréchet and the initial organic phase was prepared as a solution containing 23.75 g styrene, 8.35 g chloromethylstyrene, 2.4 g 55% DVB and 0.1 g Vazo 52, which was maintained between about 0–10° C. before copolymerization. The second procedure preferred by the applicants involved direct copolymerization of a comonomer solution of styrene and the vinyl substituted BMAP monomer. This required preparing a solution containing 11.2 g of the BMAP monomer, 18.94 g styrene, 2.37 g 55% DVB and 0.16 g Vazo 52 according to Example 2 which was also maintained between about 0–10° C. before copolymerization.

Copolymerization and Results

The copolymerization reactions in this Example were carried out using the same procedure and amounts as in Example 1. Following cooling and removal of the insoluble product by filtration, the following results were observed:

The cross linked copolymers prepared using the Tomoi aqueous phase and both organic phases yielded particles that were not uniformly spherical and varied greatly in size. The products contained a significant amount of flake and fine powders, making it very difficult to filter or recover from any commercial process. The distorted beads showed visible signs of fractures under microscopic analysis and readily broke into smaller fragments upon swelling and recapture from a toluene solvent. Similarly, severe fracturing was noted when a slurry of this material in toluene was stirred for several hours.

The cross linked copolymers prepared using the Fréchet aqueous phase and both organic phases consisted substantially of clumps of small distorted bead forms. Attempts to separate these particles resulted in substantial fracture of the discernable beads present in the material. Microscopic examination of these bead clumps revealed both fractures and many tiny bubbles and other imperfections in the particles. Similar to the Tomoi material, these copolymers also broke into smaller fragments upon repeated swelling in toluene and upon stirring in a slurry for several hours.

The cross-linked copolymers prepared using the aqueous phase of the present invention (with both organic phases) produced materials in yields over 90% by weight consisting primarily of smooth spherical beads that were hard and translucent giving all appearances of a superior gel resin structure. The beads were substantially uniform in size with minimal deviation of about 10% from the median or average bead size in each case. Little or no extraneous irregular shaped material was produced, and microscopic examination showed no signs of fractures or bubbles in the produced particles. Of equal importance, neither repeated swelling in toluene nor nondestructive stirring in a toluene slurry for more than two days resulted in any significant fracturing of the beads thereby confirming their durability for recycling in many acylation, alkylation and other related reactions of commercial significance.

What is claimed:

1. A process for preparing a cross linked polymer supported 4-(N-benzyl-N-methylamino)pyridine material in high yield having effective physical and chemical properties as a catalyst, comprising the suspension copolymerization of an organic phase containing the corresponding vinyl-substituted pyridine monomer, a styrene monomer and a suitable cross-linking agent and free radical generating catalyst in the presence of an aqueous phase containing a cellulose ether derivative as the stabilizing agent.

2. The process of claim 1 in which the cellulose ether derivative is selected from the group consisting of:
methylcellulose;
hydroxyethylcellulose;
hydroxypropylcellulose;
hydroxypropyl methylcellulose.,
hydroxyethyl methylcellulose;
carboxymethyl methylcellulose;
hydrophobically modified hydroxyethylcellulose;
carboxymethyl hydroxyethylcellulose; and
hydroxypropyl hydroxyethylcellulose.

* * * * *